United States Patent
Sato et al.

(10) Patent No.: US 8,710,184 B2
(45) Date of Patent: Apr. 29, 2014

(54) MOTILIN-LIKE PEPTIDE COMPOUND HAVING TRANSMUCOSAL ABSORBABILITY IMPARTED THERETO

(75) Inventors: Seiji Sato, Hyogo (JP); Takeshi Hanada, Hyogo (JP); Naomi Wakabayashi, Hyogo (JP); Yutaka Masuda, Hyogo (JP); Yuriko Harada, Hyogo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/388,021

(22) PCT Filed: Jul. 29, 2010

(86) PCT No.: PCT/JP2010/062746
§ 371 (c)(1),
(2), (4) Date: Jan. 30, 2012

(87) PCT Pub. No.: WO2011/013728
PCT Pub. Date: Feb. 3, 2011

(65) Prior Publication Data
US 2012/0129762 A1    May 24, 2012

(30) Foreign Application Priority Data

Jul. 29, 2009   (JP) ................. 2009-177107

(51) Int. Cl.
*A61K 38/16* (2006.01)
*A61P 1/04* (2006.01)
*A61P 1/00* (2006.01)
*C07K 14/00* (2006.01)

(52) U.S. Cl.
USPC .................... 530/326; 530/323; 514/21.4

(58) Field of Classification Search
None
See application file for complete search history.

(56) References Cited

U.S. PATENT DOCUMENTS 6,849,714 B1 * 2/2005 Bridon et al. ............ 530/335

FOREIGN PATENT DOCUMENTS

| EP | 0 378 078 | 7/1990 |
|---|---|---|
| EP | 0 507 573 | 10/1992 |
| EP | 0 646 601 | 4/1995 |
| EP | 2 548 566 | 1/2013 |
| GB | 1 507 243 | 4/1978 |
| JP | 52-046068 | 4/1977 |
| JP | 3-218395 | 9/1991 |
| JP | 7-70178 | 3/1995 |
| WO | 2011/115264 | 9/2011 |

OTHER PUBLICATIONS

Tian et al, Enhanced thermostability of methyl parathion hydrolase from *Ochrobactrum* sp. M231 by rational engineering of a glycine to proline mutation, FEBS Journal, 2010, 277, pp. 4901-4908.*
Netzer, P. et al.; "Effects of ABT-229, a Motilin Agonist, on Acid Reflux, Oesophageal Motility and Gastric Emptying in Patients with Gastro-Oesophageal Reflux Disease;" Aliment Pharmacol Ther; vol. 16, pp. 1481-1490; 2002.
Choi, Myung-Gyu et al.; "Dose-Related Effects of N-Demethyl-N-Isopropyl-8,9-anhydroerythromycin A 6,9-hemiacetal on Gastric Emptying of Solids in Healthy Human Volunteers;" The Journal of Pharmacology and Experimental Therapeutics, vol. 285, No. 1, pp. 37-40; 1998.
Stacher, G. et al.; "Erythromycin effects on gastric emptying, antral motility and plasma motilin and pancreatic polypeptide concentrations in anorexia nervosa;" Gut, vol. 34, pp. 166-172; 1993.
Janssens, J. et al.; "Improvement of gastric emptying in diabetic gastroparesis by erythromycin;" The New England Journal of Medicine; pp. 1028-1031; Apr. 12, 1990.
Peeters, T. L.; "New motilin agonists: a long and winding road;" Neurogastroenterol Motil; vol. 18, pp. 1-5; 2006.
Jenssen, T. G. et al.; "Radioimmunoassayable Plasma Motilin in Man;" Scand J. Gastroenterol, vol. 19, pp. 171-723; 1984.
Park, M. I. et al.; "Effect of atilmotin on gastrointestinal transit in healthy subjects: a randomized, placebo-controlled study;" Neurogastroenterol Motil, Vo. 18, pp. 28-36; 2006.
Kamerling, Ingrid M.C. et al.; "Motilin effects on the proximal stomach in patients with functional dyspepsia and healthy volunteers;" AJP-GI, vol. 284, pp. 776-781; 2003.
Kusano, Motoyasu et al.; "Further classification of dysmotility-like dyspepsia by interdigestive gastroduodenal manometry and plasma motilin level;" The American Journal of Gastroenterology, vol. 92, No. 3, pp. 481-484; 1997.
Labo, G. et al.; "Interdigestive gastroduodenal motility and serum motilin levels in patients with idiopathic delay in gastric emptying;" Gastroenterology, vol. 90, pp. 20-26; 1986.
Lin, Henry C.; "Small intestinal bacterial overgrowth: a framework for understanding irritable bowel syndrome;" JAMA, vol. 292, No. 7, pp. 852-858; 2004.
Castiglione, F. et al.; "Antibiotic treatment of small bowel bacterial overgrowth in patients with crohn's disease;" Aliment Pharmacol Ther.; vol. 18, pp. 1107-1112; 2003.

(Continued)

*Primary Examiner* — Julie Ha
*Assistant Examiner* — Li Ni Komatsu
(74) *Attorney, Agent, or Firm* — Hunton & Williams LLP

(57) ABSTRACT

The present invention aims at providing motilin-like peptide compounds that maintain the gastrointestinal motility stimulating activity of native motilin and which are adapted to have higher absorbability upon transmucosal administration. Motilin derivatives were designed and synthesized in consideration of the pathway for the degradation of motilin at a site of its transmucosal absorption and the maintenance of motilin's physiological activity and compounds characterized by substitutions for the amino acid at position 21 of native motilin have been found to show higher absorbability upon transmucosal administration and yet maintain the same activity as motilin.

8 Claims, 3 Drawing Sheets

(56) References Cited

OTHER PUBLICATIONS

Pardo, Albert et al.; "Effect of cisapride on intestinal bacterial overgrowth and bacterial translocation in cirrhosis;" Hepatology, vol. 31, No. 4, pp. 858-863; 2000.

Pimentel, Mark et al.; "Lower frequency of MMC is found in IBS subjects with abnormal lactulose breath test, suggesting bacterial overgrowth;" Digestive Diseases and Sciences, vol. 47, No. 12, pp. 2639-2643; Dec. 2002.

Haans, J. J. L. et al.; "Intragastric acidification inhibits motilin-induced phase III activity in humans;" Neurogastroenterol Motil, vol. 18, pp. 637-646; 2006.

Yogo, Kenji et al.; "Effects of motilin and mitemcinal (GM-611) on gastrointestinal contractile activity in rhesus monkeys in vivo and in vitro;" Dig Dis Sci; 11 pages; Nov. 7, 2006.

Nakaya, Mitsuo et al.; "Does motilin control interdigestive pepsin secretion in the dog?;" Peptides, vol. 4, pp. 439-444; 1983.

DeClercq, Peggy et al.; "Purification and amino acid sequence of human motilin isolated from a motilin containing liver metastasis;" Regulatory Peptides; vol. 55, pp. 79-84; 1995.

Schubert, Harold et al.; "Correction to the amino acid sequence of porcine motilin;" Can. J. Biochem, vol. 52, pp. 7-8; 1974.

Brown, John C. et al.; "Motilin, a gastric motor activity stimulating polypeptide: the complete amino acid sequence;" Can. J. Biochem, vol. 51; pp. 533-537; 1973.

Miller, Paul et al.; "Structure-function studies of motilin analogues;" Peptides, vol. 16, No. 1, pp. 11-18; 1995.

Boulanger, Yvan et al.; "Structural effects of the selective reduction of amide carbonyl groups in motilin 1-12 as determined by nuclear magnetic resonance;" International Journal of Peptide & Protein Research; vol. 46, pp. 527-534; 1995.

Jenssen, et al. (1984) "Radioimmunoassayable Plasma Motilin in Man;" Scand J. Gastroenterol, vol. 19, pp. 717-723.

Kusano, Motoyasu; "Non-Ulcer Dyspepsia (NUD);" MB Gastro, vol. 1, No. 3, pp. 47-56; 1991, Abstract only.

Itoh, Zen; "Motilin and its Clinical Application," Journal of the Japanese Society of Gastrogenterology; vol. 93, pp. 517-529; 1996, Only the first page, Part I.

* cited by examiner

SEQUENCE LISTING

```
<160> NUMBER OF SEQ ID NOS: 17

<210> SEQ ID NO 1
<211> LENGTH: 22
<212> TYPE: PRT
<213> ORGANISM: Homo sapiens

<400> SEQUENCE: 1

Phe Val Pro Ile Phe Thr Tyr Gly Glu Leu Gln Arg Met Gln Glu Lys
1               5                   10                  15

Glu Arg Asn Lys Gly Gln
            20

<210> SEQ ID NO 2
<211> LENGTH: 22
<212> TYPE: PRT
<213> ORGANISM: Artificial Sequence
<220> FEATURE:
<223> OTHER INFORMATION: Amino acid sequence of Motilin homologues.
<220> FEATURE:
<221> NAME/KEY: MISC_FEATURE
<222> LOCATION: (1)..(1)
<223> OTHER INFORMATION: an aromatic amino acid or a heterocyclic
      aromatic amino acid
<220> FEATURE:
<221> NAME/KEY: MISC_FEATURE
<222> LOCATION: (3)..(3)
<223> OTHER INFORMATION: proline or sarcosine (Sar; or N-methylglycine,
      MeGly)
<220> FEATURE:
<221> NAME/KEY: MISC_FEATURE
<222> LOCATION: (9)..(9)
<223> OTHER INFORMATION: aspartic acid or glutamic acid
<220> FEATURE:
<221> NAME/KEY: MISC_FEATURE
<222> LOCATION: (13)..(13)
<223> OTHER INFORMATION: methionine or leucine
<220> FEATURE:
<221> NAME/KEY: MISC_FEATURE
<222> LOCATION: (19)..(19)
<223> OTHER INFORMATION: proline or asparagine
```

-continued

```
<400> SEQUENCE: 2

Xaa Val Xaa Ile Phe Thr Tyr Gly Xaa Leu Gln Arg Xaa Gln Glu Lys
1               5                   10                  15

Glu Arg Xaa Lys Pro Gln
            20

<210> SEQ ID NO 3
<211> LENGTH: 22
<212> TYPE: PRT
<213> ORGANISM: Artificial Sequence
<220> FEATURE:
<223> OTHER INFORMATION: Amino acid sequence of Compound 1 (MT095).

<400> SEQUENCE: 3

Phe Val Pro Ile Phe Thr Tyr Gly Glu Leu Gln Arg Met Gln Glu Lys
1               5                   10                  15

Glu Arg Asn Lys Pro Gln
            20

<210> SEQ ID NO 4
<211> LENGTH: 22
<212> TYPE: PRT
<213> ORGANISM: Artificial Sequence
<220> FEATURE:
<223> OTHER INFORMATION: Amino acid sequence of Compound 2 (MT114).

<400> SEQUENCE: 4

Phe Val Pro Ile Phe Thr Tyr Gly Glu Leu Gln Arg Leu Gln Glu Lys
1               5                   10                  15

Glu Arg Asn Lys Pro Gln
            20

<210> SEQ ID NO 5
<211> LENGTH: 22
<212> TYPE: PRT
<213> ORGANISM: Artificial Sequence
<220> FEATURE:
<223> OTHER INFORMATION: Amino acid sequence of Compound 3 (MT116).

<400> SEQUENCE: 5

Phe Val Pro Ile Phe Thr Tyr Gly Asp Leu Gln Arg Leu Gln Glu Lys
1               5                   10                  15

Glu Arg Pro Lys Pro Gln
            20

<210> SEQ ID NO 6
<211> LENGTH: 22
<212> TYPE: PRT
<213> ORGANISM: Artificial Sequence
<220> FEATURE:
<223> OTHER INFORMATION: Amino acid sequence of Compound 4 (MT124).
<220> FEATURE:
<221> NAME/KEY: MISC_FEATURE
<222> LOCATION: (1)..(1)
<223> OTHER INFORMATION: beta-homophenylglycine (Phg(C#CH2))

<400> SEQUENCE: 6

Xaa Val Pro Ile Phe Thr Tyr Gly Glu Leu Gln Arg Leu Gln Glu Lys
1               5                   10                  15

Glu Arg Pro Lys Pro Gln
            20

<210> SEQ ID NO 7
<211> LENGTH: 22
<212> TYPE: PRT
```

```
<213> ORGANISM: Artificial Sequence
<220> FEATURE:
<223> OTHER INFORMATION: Amino acid sequence of Compound 5 (MT126).
<220> FEATURE:
<221> NAME/KEY: MISC_FEATURE
<222> LOCATION: (1)..(1)
<223> OTHER INFORMATION: beta-homophenylglycine (Phg(C#CH2))
<220> FEATURE:
<221> NAME/KEY: MISC_FEATURE
<222> LOCATION: (3)..(3)
<223> OTHER INFORMATION: sarcosine (Sar; or N-methylglycine, MeGly)

<400> SEQUENCE: 7

Xaa Val Xaa Ile Phe Thr Tyr Gly Glu Leu Gln Arg Leu Gln Glu Lys
1               5                   10                  15

Glu Arg Pro Lys Pro Gln
            20

<210> SEQ ID NO 8
<211> LENGTH: 22
<212> TYPE: PRT
<213> ORGANISM: Artificial Sequence
<220> FEATURE:
<223> OTHER INFORMATION: Amino acid sequence of Compound 6 (MT140).

<400> SEQUENCE: 8

Phe Val Pro Ile Phe Thr Tyr Gly Glu Leu Gln Arg Met Gln Glu Lys
1               5                   10                  15

Glu Arg Asn Lys Pro Gln
            20

<210> SEQ ID NO 9
<211> LENGTH: 22
<212> TYPE: PRT
<213> ORGANISM: Artificial Sequence
<220> FEATURE:
<223> OTHER INFORMATION: Amino acid sequence of Compound 7 (MT141).

<400> SEQUENCE: 9

Phe Val Pro Ile Phe Thr Tyr Gly Glu Leu Gln Arg Leu Gln Glu Lys
1               5                   10                  15

Glu Arg Asn Lys Pro Gln
            20

<210> SEQ ID NO 10
<211> LENGTH: 22
<212> TYPE: PRT
<213> ORGANISM: Artificial Sequence
<220> FEATURE:
<223> OTHER INFORMATION: Amino acid sequence of Compound 8 (MT107).

<400> SEQUENCE: 10

Phe Val Pro Ile Phe Thr Tyr Gly Glu Leu Gln Arg Met Gln Glu Lys
1               5                   10                  15

Glu Arg Pro Lys Pro Gln
            20

<210> SEQ ID NO 11
<211> LENGTH: 22
<212> TYPE: PRT
<213> ORGANISM: Artificial Sequence
<220> FEATURE:
<223> OTHER INFORMATION: Amino acid sequence of Compound 9 (MT115).

<400> SEQUENCE: 11

Phe Val Pro Ile Phe Thr Tyr Gly Glu Leu Gln Arg Leu Gln Glu Lys
1               5                   10                  15
```

```
<210> SEQ ID NO 12
<211> LENGTH: 22
<212> TYPE: PRT
<213> ORGANISM: Artificial Sequence
<220> FEATURE:
<223> OTHER INFORMATION: Amino acid sequence of Compound 10 (MT125).
<220> FEATURE:
<221> NAME/KEY: MISC_FEATURE
<222> LOCATION: (1)..(1)
<223> OTHER INFORMATION: beta-homophenylglycine (Phg(C#CH2))
<220> FEATURE:
<221> NAME/KEY: MISC_FEATURE
<222> LOCATION: (3)..(3)
<223> OTHER INFORMATION: sarcosine (Sar; or N-methylglycine, MeGly)

<400> SEQUENCE: 12

Xaa Val Xaa Ile Phe Thr Tyr Gly Glu Leu Gln Arg Met Gln Glu Lys
1               5                   10                  15

Glu Arg Pro Lys Pro Gln
            20

<210> SEQ ID NO 13
<211> LENGTH: 22
<212> TYPE: PRT
<213> ORGANISM: Artificial Sequence
<220> FEATURE:
<223> OTHER INFORMATION: Amino acid sequence of Compound 11 (MT128).
<220> FEATURE:
<221> NAME/KEY: MISC_FEATURE
<222> LOCATION: (1)..(1)
<223> OTHER INFORMATION: acetylnaphthylalanine (Ac-Nal)

<400> SEQUENCE: 13

Xaa Val Pro Ile Phe Thr Tyr Gly Glu Leu Gln Arg Met Gln Glu Lys
1               5                   10                  15

Glu Arg Asn Lys Pro Gln
            20

<210> SEQ ID NO 14
<211> LENGTH: 22
<212> TYPE: PRT
<213> ORGANISM: Artificial Sequence
<220> FEATURE:
<223> OTHER INFORMATION: Amino acid sequence of Compound 12 (MT154).

<400> SEQUENCE: 14

Phe Val Pro Ile Phe Thr Tyr Gly Asp Leu Gln Arg Leu Gln Glu Lys
1               5                   10                  15

Glu Arg Pro Lys Pro Gln
            20

<210> SEQ ID NO 15
<211> LENGTH: 22
<212> TYPE: PRT
<213> ORGANISM: Artificial Sequence
<220> FEATURE:
<223> OTHER INFORMATION: Amino acid sequence of Compound 13 (MT155).

<400> SEQUENCE: 15

Phe Val Pro Ile Phe Thr Tyr Gly Asp Leu Gln Arg Met Gln Glu Lys
1               5                   10                  15

Glu Arg Pro Lys Pro Gln
            20
```

```
<210> SEQ ID NO 16
<211> LENGTH: 22
<212> TYPE: PRT
<213> ORGANISM: Artificial Sequence
<220> FEATURE:
<223> OTHER INFORMATION: Amino acid sequence of Reference Compound 1
      (13Leu-Motilin).

<400> SEQUENCE: 16

Phe Val Pro Ile Phe Thr Tyr Gly Glu Leu Gln Arg Leu Gln Glu Lys
1               5                   10                  15

Glu Arg Asn Lys Gly Gln
            20

<210> SEQ ID NO 17
<211> LENGTH: 22
<212> TYPE: PRT
<213> ORGANISM: Artificial Sequence
<220> FEATURE:
<223> OTHER INFORMATION: Amino acid sequence of Reference Compound 2
      (MT139).

<400> SEQUENCE: 17

Phe Val Pro Ile Phe Thr Tyr Gly Glu Leu Gln Arg Met Gln Glu Lys
1               5                   10                  15

Glu Arg Asn Lys Gly Gln
            20
```

MOTILIN-LIKE PEPTIDE COMPOUND HAVING TRANSMUCOSAL ABSORBABILITY IMPARTED THERETO

CROSS-REFERENCE TO RELATED APPLICATIONS

This is the U.S. National Stage application of International Patent Application No. PCT/JP2010/062746, filed Jul. 29, 2010, which claims priority to JP 177107/2009, filed Jul. 29, 2009, the disclosures of each of which are hereby incorporated by reference in their entirety.

TECHNICAL FIELD

The present invention relates to motilin-like peptide compounds that have such a higher activity on stimulation of gastrointestinal motility and higher absorbability upon transmucosal administration that are useful in the treatment of conditions characterized by functional abnormalities in the gastrointestinal tract, such as functional dyspepsia, diabetic gastroparesis, gastroesophageal reflux disease, irritable bowel syndrome, small intestinal bacterial overgrowth, colonic pseudo-obstruction, paralytic ileus, chronic idiopathic intestinal pseudo-obstruction, and post-operative ileus.

BACKGROUND ART

Motilin is a physiologically active peptide of 22 amino acids isolated from the abdominal smooth muscle and its structure was first identified in 1973 by isolation of porcine motilin (Non-Patent Documents 1 and 2). In 1995, human motilin was isolated and identified to have the same structure as the porcine motilin (Non-Patent Document 3).

Motilin is known to have a physiological function that is associated with the interdigestive migrating complex (hereinafter abbreviated as IMC) which occurs in a fasting stage. IMC is a physiological function by which the contents of the gastrointestinal tract such as the epithelium and mucous membrane that have been peeled off from its internal wall, as well as the secretory fluids therefrom are forced to flow down to its lower part, thereby cleaning up its interior. In healthy persons, motilin is secreted from the duodenum and jejunum at approximately 100-min intervals in a fasting stage, with IMC occurring with an increase in the plasma motilin level (Non-Patent Document 4); IMC is induced when motilin is administered to a dog, monkey, or a human (Non-Patent Documents, 5, 6 and 7); physiological IMC occurrence is suppressed by administering anti-motilin serum; in view of these and other findings, it is held that gastrointestinal functions such as the digestion of foods and the secretion of digestive juice are maintained normally as the result of motilin secretion which induces IMC, causing the debris to be removed from within the gastrointestinal tract (Non-Patent Document 8).

Regarding the relations between IMC abnormality and a disease, it has been reported that, when IMC is reduced, the debris within the gastrointestinal tract accumulates within the intestinal tract to cause an abnormal growth of intestinal bacteria, whereupon endotoxins are produced by the intestinal bacteria to induce gastrointestinal conditions such as excessive evolution of gas, abdominal bloating, diarrhea, and abdominal pain (Non-Patent Document 9). Particularly in diseases that are associated with functional abnormalities in the gastrointestinal tract, such as functional dyspepsia, post-operative ileus, and chronic idiopathic intestinal pseudo-obstruction, it has been reported that IMC occurrence is reduced or not observed at all (Non-Patent Document 13) and that a decrease in the secretion of endogenous motilin in vivo or a decrease in the motilin action is related to abnormalities or reduction in the gastrointestinal motility functions (Non-Patent Document 14). Irritable bowel syndrome is a chronic intestinal disorder which, in the absence of any underlying diseases such as inflammations and tumors but on account of functional abnormalities in the lower gastrointestinal tract, typically the large intestine, causes chronic abdominal discomfort as exemplified by abdominal pain and abdominal bloating, or bowel movement abnormalities such as constipation and diarrhea. It has been reported that in at least some of the patients who developed irritable bowel syndrome, the intestinal flora had altered to cause a change in bacterial species, abnormal bacterial growth, etc. (Non-Patent Document 9) and the accumulation of the gastrointestinal debris within the intestinal tract on account of reduced occurrence of IMC may be a cause of the change in the intestinal flora.

The currently available drugs of first choice against diseases associated with the aforementioned functional abnormalities in the gastrointestinal tract are medicines for internal use to improve gastrointestinal motility function, as exemplified by dopamine receptor antagonists, selective serotonin 5-HT4 receptor agonists, and parasympathetic stimulating agents. There are indeed some cases where treatment with these therapeutic drugs showed a temporary improvement of the symptoms but in many other cases, no therapeutic effect was observed and doctors and patients are getting only low satisfaction from those internal medicines used to improve gastrointestinal motility. Therefore, it is strongly desired to provide therapeutics based on a new mechanism of action and it is expected to lead to amelioration of the symptoms or curing of the disease by externally administering motilin receptor agonists to patients with functional abnormalities in the gastrointestinal tract so as to normalize their gastrointestinal functions.

Ever since it was reported that erythromycin and its related compounds have an activity as motilin agonists, clinical trials have been conducted with low-molecular weight motilin agonists on patients with functional abnormalities in the gastrointestinal tract (Non-Patent Documents 19 and 20) and there are also a plurality of such low-molecular weight motilin agonists that were subjected to clinical trials as oral drugs (Non-Patent Documents 21 and 22). However, for one or another reason such as the development of side-effects that have nothing to do with the action as motilin agonists (i.e., HERG inhibition, spermatogenic defect, and carcinogenic effect) or the attenuation of the drug efficacy due to repeated administration, the development of pharmaceuticals containing the motilin agonists as the active ingredient has been suspended and none of them have so far been put on the market as medicines for improving gastrointestinal functions.

Clinical trials were also performed on patients with functional abnormalities in the gastrointestinal tract, using native motilin or peptide motilin agonists as peptide compounds (Non-Patent Documents 15 and 16). However, the only route of administration that has ever been reported in connection with the clinical trials and animal experiments using these peptide compounds is an intravenous one and on account of the difficulty in realizing prolonged, repeated administration to patients, the therapeutic efficacy of the compounds is yet to be verified.

Examples of motilin-like peptide compounds that have so far been developed are atilmotin of Baxter (Patent Document 1) and SK-896 of SANWA KAGAKU (Patent Document 2). The former is a compound created with a view to improving the in vivo half-life and by means of a metabolism experiment using a homogenate supernatant of the kidney which is conceived as a primary organ for motilin metabolism (Non-Patent Document 17), the compound has been verified to have better metabolic stability (Patent Document 1) and its half-life in plasma is about 10 minutes, approximately three times as long as that of motilin (Non-Patent Document 18). The latter is a compound designed to realize more efficient production. Both compounds maintain a gastrointestinal motility enhancing activity comparable to that of motilin. However, as in the case of motilin, the route of administration of these compounds is limited to an intravenous one and each compound has the problem that its use is limited to the treatment in medical facilities where it cannot be used for a prolonged period of time. Hence, there has been accomplished no drug discovery that is based on the inherent action of motilin, i.e., maintaining the gastrointestinal functions in a normal way by removing the debris from the inside of the gastrointestinal tract, with the result that the therapeutic efficacy of either compound is yet to be verified.

A peptide having a substitution of leucine for methionine at position 13 of motilin has been developed (Patent Document 3). However, the biological activity of this peptide is comparable to that of motilin and the route of its administration is limited to an intravenous one, thus leaving the problem of impossibility of prolonged use still unsolved.

In view of the foregoing, it is desired that in order to develop a novel therapeutic drug based on the inherent action of motilin, a peptidic motilin agonist should be provided as a pharmaceutical agent that can be administered for a prolonged period of time via a noninvasive route.

CITATION LIST

Patent Reference

Patent Document 1: JP Hei 7-70178 A
Patent Document 2: JP Hei 7-42319 B
Patent Document 3: JP Sho 52-46068 A Non-Patent Reference Non-Patent Document 1: Brown J et al., Can J Biochem, 51, 533 (1973)
Non-Patent Document 2: Schubert H et al., Can J Biochem, 52, 7 (1974)
Non-Patent Document 3: De Clercq et al., Regul Pept, 55, 79 (1995)
Non-Patent Document 4: Itoh, Nisshoushi (Journal of the Japanese Society of Gastrogenterology) 93, 517 (1996)
Non-Patent Document 5: Nakaya M et al., Peptides, 4, 439 (1983)
Non-Patent Document 6: Yogo K et al., Dig Dis Sci, 52, 3112 (2007)
Non-Patent Document 7: Haans J et al., Neurogastroenterol Motil, 18, 637 (2006)
Non-Patent Document 8: Kusano et al, MB Gastro, 1, 47 (1991)
Non-Patent Document 9: Pimentel M et al., Dig Dis Sci, 47, 2639 (2002)
Non-Patent Document 10: Pardo A et al., Hepatology 31, 858 (2000)
Non-Patent Document 11: Castiglione F et al., Aliment Pharmacol Ther. 18, 1107 (2003)
Non-Patent Document 12: Henry C. Lin, JAMA. 292, 852 (2004)
Non-Patent Document 13: Labo G et al., Gastroenterology, 90, 20 (1986)
Non-Patent Document 14: Kusano M et al., Am J Gastroenterol, 92, 481 (1997)
Non-Patent Document 15: Kamerling I et al., Am J Physiol Gastrointest Liver Physiol, 284, G776 (2003)
Non-Patent Document 16: Park M-I et al., Neurogastroenterol Motil, 18, 28 (2006)
Non-Patent Document 17: Jenssen T G et al., Scand J Gastroenterol, 19, 717 (1984)
Non-Patent Document 18: Peeters T L et al., Neurogastroenterol Motil, 18, 1 (2006)
Non-Patent Document 19: Janssens J et al., N Engl J Med, 322, 1028 (1990)
Non-Patent Document 20: Stacher G et al., Gut, 34, 166 (1993)
Non-Patent Document 21: Choi M G et al., J Pharmacol Exp Ther, 285, 37 (1998)
Non-Patent Document 22: Netzer P et al., Aliment Pharmacol Ther, 16, 1481 (2002)

SUMMARY OF INVENTION

Technical Problem

A problem of the present invention is to provide motilin-like peptide compounds that maintain the gastrointestinal motility stimulating activity of native motilin and which are adapted to have higher absorbability upon transmucosal administration.

Solution to Problem

To solve this problem, the present inventors first assumed that motilin might be degraded after noninvasive transmucosal administration and performed a motilin degradation experiment using a lung homogenate supernatant. As a result, motilin was found to be degraded and by identifying the degradation product, the pathway of motilin degradation was estimated to be such that its C terminal would undergo degradation by dicarboxy peptidase.

Based on these results, the present inventors substituted proline for glycine at position 21 of motilin so that the dicarboxy peptidase mediated degradation of the C terminal would be inhibited to produce motilin-like peptide compounds showing higher absorbability upon transmucosal administration, which led to the accomplishment of the present invention. In addition, since the N terminal side of phenylalanine was found to undergo degradation, it was shown that replacing the amide bond between the first and the second amino acids from the N terminal by a non-peptide bond, -psi [CH$_2$NH]— bond, would also contribute to a further improvement in metabolic stability.

(i) Specifically, the present invention has revealed that the above-stated problem can be attained by preparing peptide compounds that maintain a gastrointestinal motility stimulating activity comparable to that of native motilin and which yet have higher absorbability upon transmucosal administration, said compounds being compounds comprising the sequence represented by the following formula 1 which is characterized by a substitution with proline at the 21th position amino acid:

(formula 1)
(SEQ ID NO: 2)
X1 Val X2 Ile Phe Thr Tyr Gly X3 Leu Gln Arg X4

Gln Glu Lys Glu Arg X5 Lys Pro Gln

[wherein all bonds between amino acids, other than the X1-Val bond, are amide bonds;

X1 is an aromatic amino acid or a heteroaromatic amino acid;

the X1-Val bond is an amide bond or a bond represented by the following formula 2

(formula 2)

$$N_{terminal}-\underset{H}{\overset{H}{\underset{|}{C}}}-\underset{}{\overset{H}{\underset{|}{N}}}-C_{terminal}$$

X2 is proline or sarcosine;
X3 is glutamic acid or aspartic acid;
X4 is methionine or leucine;
X5 is asparagine or proline]
or pharmaceutically acceptable salts thereof.

The present invention further encompasses the following:
(ii) The compound or pharmaceutically acceptable salt thereof as recited in (i), wherein X1 in formula 1 is an α-amino acid such as phenylalanine (Phe), tyrosine (Tyr), or tryptophan (Trp), or β-homophenylglycine (Phg (C#CH$_2$)) or acetylnaphthylalanine (Ac-Nal).
(iii) The compound or pharmaceutically acceptable salt thereof as recited in (ii), wherein X1 in formula 1 is phenylalanine (Phe) or β-homophenylglycine.
(iv) A compound which is depicted by the sequence selected from the group consisting of SEQ ID NOS: 3 to 15 or a pharmaceutically acceptable salt thereof.
(v) A compound which is depicted by SEQ ID NO: 4 or a pharmaceutically acceptable salt thereof.
(vi) A compound which is depicted by SEQ ID NO: 6 or a pharmaceutically acceptable salt thereof.
(vii) A compound which is depicted by SEQ ID NO: 8 or a pharmaceutically acceptable salt thereof.
(viii) A pharmaceutical composition for the treatment of a disease associated with a functional abnormality in the gastrointestinal tract, which comprises the peptide compound or pharmaceutically acceptable salt thereof as recited in any one of (i) to (vii).
(ix) The pharmaceutical composition as recited in (viii), wherein the disease associated with a functional abnormality in the gastrointestinal tract involves a drop in the baseline of gastrointestinal motility activity.
(x) The pharmaceutical composition as recited in (viii) wherein the disease associated with a functional abnormality in the gastrointestinal tract is functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, or post-operative ileus.
(xi) The pharmaceutical composition as recited in any one of (viii) to (x) which is intended for transmucosal administration.
(xii) The pharmaceutical composition as recited in (xi) wherein the transmucosal administration is pulmonary or intranasal administration.
(xiii) The pharmaceutical composition as recited in (xii) wherein the transmucosal administration is intranasal administration.
(xiv) A method of treating conditions characterized by a drop in the baseline of gastrointestinal motility activity, such as functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, and post-operative ileus, the method comprising administering the pharmaceutical composition as recited in (viii) to an individual.

ADVANTAGEOUS EFFECTS OF DRAWINGS

The novel motilin-like peptide compounds according to the present invention have the motilin-like gastrointestinal motility stimulating activity and show higher absorption efficiency upon transmucosal administration. Therefore, the compounds of the present invention can be used to treat diseases associated with functional abnormalities in the gastrointestinal tract (for example, conditions characterized by a drop in the baseline of gastrointestinal motility activity.) Diseases associated with functional abnormalities in the gastrointestinal tract include conditions such as functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, and post-operative ileus. In addition, the compounds of the present invention have higher absorption efficiency than native motilin upon transmucosal administration, and need be administered in lower doses to attain plasma concentrations effective for the treatment of patients.

DESCRIPTION OF EMBODIMENTS

Figure 1:
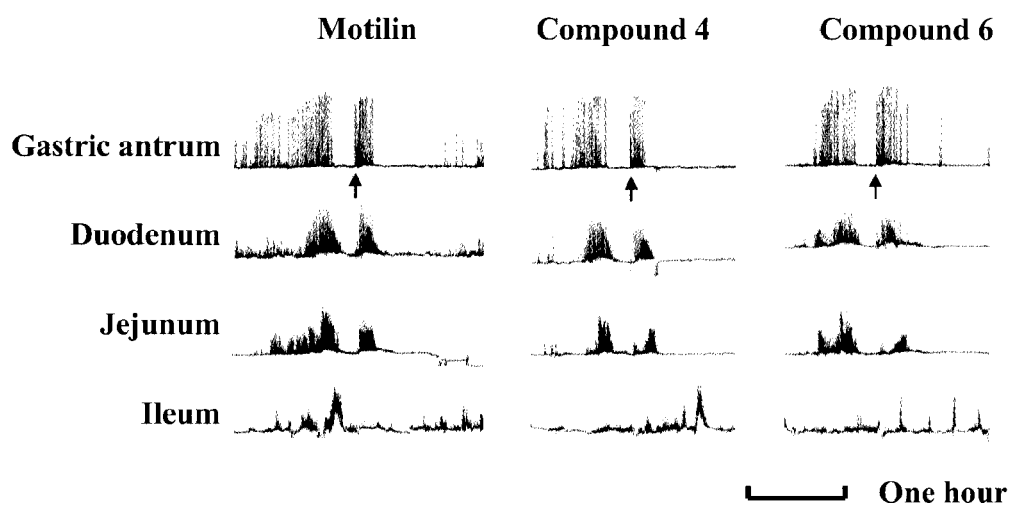
FIG. 1 is a graph showing the fasting IMC inducing activity as exhibited when native motilin, compound 4 and compound 6 were administered intravenously.

Native motilin is known to have the N-terminal portion as an essential site for developing its activity, and it is also known that while native motilin forms an α-helical structure in solution in a C terminal region extending from the vicinity of the 6th-position threonine [Andersson A. & Maler L., J. Biomol. NMR, 24, 103-112 (2002)], derivatives having mutations introduced into the α-helical structure which is away from the active center are reduced in their ability to activate the receptor [Miller P et al., Peptides, 16, 11-18 (1995)]. Based on the findings provided in these documents, the present inventors assumed that the α-helical structure would contribute to stabilizing the active center at the N terminal. In other words, they thought that the presence of the α-helical structure would serve to protect the structure of the active center at the N terminal.

Therefore, when effecting structural modifications that would interrupt the pathway of motilin degradation, the present inventors selected sites that would be independent of a possible drop in activity that might result from destabilization of the α-helical structure.

The 1st-position amino acid at the N terminal of motilin (which is hereinafter referred to as X1) is essential for activating the receptor and hence desirably protected against degradation. The present inventors thought that in order to confer resistance to the degradative enzyme, extending the distance from the N-terminal amino group to the X1-Val peptide bond or replacing the X1-Val peptide bond with a non-amide bond would be useful for acquisition of resistance to degradation.

In addition, X2 in native motilin is proline and defines the conformational structure of the compound, so the present inventors thought that by enhancing its degree of freedom, it might be possible to control the receptor activating ability. In native motilin, X3 is glutamic acid and forms a hydrogen bond with a side chain between the 6th-position threonine, apparently contributing to the formation of the α-helical structure in the region extending from the 6th-position toward the C terminal end [Andersson A. & Maler L. J. Biomol. NMR, 24, 103-112 (2002)]. Since it is known that a substitution of X3 with alanine or D-glutamic acid caused a substantial drop in the receptor activating ability [Miller P. et al., Peptides, 16, 11-18 (1995), and Peeters T. L., et al., Peptides, 13, 1103-1107 (1992)], X3 is desirably selected from L-acidic amino acids. As for X4, it is methionine in native motilin and will reduce the receptor activating ability by the side chain oxidation. Hence, methionine is desirably replaced by leucine which is substantially comparable to it in terms of the size of the side chain.

Motilin is degraded by dicarboxy peptidase, starting from the C terminal end. The present inventors thought that substituting amino acids with proline on the C terminal side of native motilin would fix the dihedral angle around the peptide bond and offer resistance to degradation by virtue of steric hindrance that will accompany coordination to the substrate-binding site at which dicarboxy peptidase binds the substrate or to the active center.

On the other hand, since the α-helical structure of motilin is important for the receptor activating capability, those sites for substitution of proline which make it difficult for motilin to form the α-helical structure are considered to be limited. From these viewpoints, the present inventors conceived of a substitution of X5 and/or the 21-position amino acid with proline.

It was from such viewpoints that the present inventors designed and synthesized derivatives and subjected them to a degradation experiment using a lung homogenate supernatant and a contraction experiment using an extracted intestinal tract. A series of motilin-like peptide compounds according to the present invention that had a substitution of glycine at position 21 of motilin with proline were subjected to an experiment for transmucosal administration in vivo, whereby the present inventors confirmed that those compounds showed higher absorbability than native motilin and yet maintaining IMC inducing activity comparable to that of the native motilin; the present invention has been accomplished on the basis of this finding.

The peptide compounds of the present invention are compounds comprising the sequence represented by the following general formula 1 which is characterized by a substitution of proline for the 21-position amino acid:

```
(formula 1)
                                        (SEQ ID NO: 2)
X1 Val X2 Ile Phe Thr Tyr Gly X3 Leu Gln Arg X4

Gln Glu Lys Glu Arg X5 Lys Pro Gln
```

[wherein all bonds between amino acids, other than the X1-Val bond, are amide bonds;

the X1-Val bond is an amide bond or a bond represented by the following formula 2

$$N_{terminal}-\overset{H}{\underset{H}{\overset{|}{C}}}-\overset{H}{\underset{}{\overset{|}{N}}}-C_{terminal}$$ (formula 2)

X1 is an aromatic amino acid or a heteroaromatic amino acid;

X2 is proline or sarcosine;

X3 is glutamic acid or aspartic acid;

X4 is methionine or leucine;

X5 is asparagine or proline]

or pharmaceutically acceptable salts thereof, and they are characterized by maintaining a gastrointestinal motility stimulating activity comparable to that of native motilin and yet having higher absorbability upon transmucosal administration.

In above formula 1, X1 is an aromatic amino acid or a heteroaromatic amino acid. The aromatic amino acid or heteroaromatic amino acid refers to any amino acid that contains an aromatic ring in the it and examples include, for example, α-amino acids such as phenylalanine (Phe), tyrosine (Tyr), and tryptophan (Trp), as well as or β-homophenylglycine (Phg(C#CH$_2$)), acetylnaphthylalanine (Ac-Nal), and the like. In the present invention, phenylalanine (Phe), β-homophenylglycine (Phg(C#CH$_2$)) and acetylnaphthylalanine (Ac-Nal) may be mentioned as more preferred examples of the amino acid X1.

In above formula 1, X1 may be an L-amino acid or a D-amino acid. In the prior art, variants have so far been prepared by substituting L-amino acids with D-amino acids as the amino acid at position 1 of motilin (Miller P. et al., Peptides, 16, 11-18 (1995)) and those variants have been shown to maintain the activity of motilin.

In above formula 1, X2 is proline (Pro) or sarcosine (Sar, also called N-methylglycine or MeGly); X3 is glutamic acid (Glu) or aspartic acid (Asp); X4 is methionine (Met) or leucine (Leu); and X5 is asparagine (Asn) or proline (Pro). The amino acids labeled X1 to X5 may be used in any combinations.

In the peptide compounds of above formula 1, the bond between the first amino acid (X1) and the second amino acid (Val) is an amide bond or a bond represented by the following formula 2

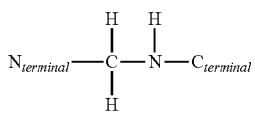
(formula 2)

The bond of formula 2 is also called a -psi[CH$_2$NH]- bond. The X1-Val bond may be either an amide bond or the -psi[CH$_2$NH]- bond irrespective of the type of the amino acid that constitutes X1.

The compounds of above formula 1 of the present invention include, for example, the compounds depicted by the following sequences or pharmaceutically acceptable salts thereof.

```
                                               (SEQ ID NO: 3)
Phe Val Pro Ile Phe Thr Tyr Gly Glu Leu Gln Arg

Met Gln Glu Lys Glu Arg Asn Lys Pro Gln;

(SEQ ID NO: 4)
Phe Val Pro Ile Phe Thr Tyr Gly Glu Leu Gln Arg

Leu Gln Glu Lys Glu Arg Asn Lys Pro Gln;

(SEQ ID NO: 5)
Phe Val Pro Ile Phe Thr Tyr Gly Asp Leu Gln Arg

Leu Gln Glu Lys Glu Arg Pro Lys Pro Gln;

(SEQ ID NO: 6)
Phg(C#CH₂) Val Pro Ile Phe Thr Tyr Gly Glu Leu

Gln Arg Leu Gln Glu Lys Glu Arg Pro Lys Pro Gln;

(SEQ ID NO: 7)
Phg(C#CH₂) Val Sar Ile Phe Thr Tyr Gly Glu Leu

Gln Arg Leu Gln Glu Lys Glu Arg Pro Lys Pro Gln;

(SEQ ID NO: 8)
Phe Val Pro Ile Phe Thr Tyr Gly Glu Leu Gln Arg

Met Gln Glu Lys Glu Arg Asn Lys Pro Gln;

(SEQ ID NO: 9)
Phe Val Pro Ile Phe Thr Tyr Gly Glu Leu Gln Arg

Leu Gln Glu Lys Glu Arg Asn Lys Pro Gln;

(SEQ ID NO: 10)
Phe Val Pro Ile Phe Thr Tyr Gly Glu Leu Gln Arg

Met Gln Glu Lys Glu Arg Pro Lys Pro Gln;

(SEQ ID NO: 11)
Phe Val Pro Ile Phe Thr Tyr Gly Glu Leu Gln Arg

Leu Gln Glu Lys Glu Arg Pro Lys Pro Gln;

(SEQ ID NO: 12)
Phg(C#CH₂) Val Sar Ile Phe Thr Tyr Gly Glu Leu

Gln Arg Met Gln Glu Lys Glu Arg Pro Lys Pro Gln;

(SEQ ID NO: 13)
Ac-Nal Val Pro Ile Phe Thr Tyr Gly Glu Leu Gln

Arg Met Gln Glu Lys Glu Arg Asn Lys Pro Gln;

(SEQ ID NO: 14)
Phe Val Pro Ile Phe Thr Tyr Gly Asp Leu Gln Arg

Leu Gln Glu Lys Glu Arg Pro Lys Pro Gln;

(SEQ ID NO: 15)
Phe Val Pro Ile Phe Thr Tyr Gly Asp Leu Gln Arg

Met Gln Glu Lys Glu Arg Pro Lys Pro Gln.
```

The compounds according to the present invention can be obtained by conventional methods. For example, they can be produced by chemical synthesis, recombinant DNA technology (in the case of peptides solely composed of L-amino acids), or combinations thereof.

Various methods have already been established for chemical synthesis of peptides and the compounds of the present invention can also be produced easily by known methods. For example, classical peptide synthesis methods and solid-phase methods can be employed. Specifically, amino acids with protective groups are concentrated by a liquid-phase method and/or a solid-phase method, then the peptide chain is extended and after optionally cleaving the N-terminal protective group with a base such as piperazine, all protective groups and resin are removed with an acid and the resulting crude product is purified by a separating/purifying procedure such as gel filtration, ultrafiltration, dialysis, SDS-PAGE, or various chromatographic techniques, whereupon the peptides of the present invention can be obtained. For example, they can be produced by the methods described in books such as "Seikagaku Jikken Koza 1 Tanpakushitu no Kagaku (Course of Biochemical Experimentation 1, Chemistry of Protein)," Vol. 4, Chapters 2 and 3 (written in Japanese, Tokyo Kagaku Dojin) and "Zoku Iyakuhinn no Kaihatsu 14 Peptide Gosei (Drug Development 14, Sequel Version, Peptide Synthesis)" (written in Japanese, Hirokawa Shoten).

Among the compounds of the present invention, the ones having the -psi[CH$_2$NH]— bond of formula 2 as a bond between amino acids can also be obtained by chemical synthesis. For example, in the case of synthesizing a compound in which the X1-Val bond in formula 1 is the -psi[CH$_2$NH]— bond, the above-described method is applied to extend the peptide chain from the C terminal to the 2-position amino acid (Val in formula 1) and then the protective group on the α-amino group in the 2-position amino acid is cleaved chemically; thereafter, Boc- or Fmoc-amino acid aldehyde is introduced by reductive alkylation reaction with sodium cyanotrihydroborate/1% acetic acid, followed by resin removal and deprotection with an acid in the same way as described above to obtain a crude product, which is subsequently purified by a separating/purifying procedure such as gel filtration, ultrafiltration, dialysis, SDS-PAGE, or various chromatographic techniques, whereupon the desired peptide analogs of the present invention can be obtained.

Peptides solely composed of L-form natural amino acids can be produced by recombinant DNA technology. Specifically, a host cell transformed with an expression vector having DNA coding for the peptide sequence according to the present invention can be cultured to harvest the desired peptide from the resulting culture.

Examples of the vector into which the gene is to be incorporated include E. coli vectors (e.g. pBR322, pUC18, and pUC19), B. subtilis vectors (e.g. pUB110, pTP5, and pC194), yeast vectors (e.g. YEp, YRp, and YIp types), and animal cell vectors (e.g. retrovirus and vaccinia virus) but any other vectors can be used as long as they are capable of retaining the desired gene stably within the host cell. The vector of interest is introduced into a suitable host cell. Various methods can be utilized to incorporate the desired gene into a plasmid or to introduce it into a host cell and exemplary methods are described in Molecular Cloning (Sambrook et al., 1989).

To express the desired peptide gene in the plasmid mentioned above, a promoter is functionally linked upstream of that gene. Any promoters can be used in the present invention as long as they are appropriate for the host cell that is used to express the desired gene. For example, if the host cell to be transformed is of the genus *Escherichia*, a lac promoter, a trp promoter, an lpp promoter, a λPL promoter, a recA promoter, etc. may be used; in the case of the genus *Bacillus*, an SP01 promoter, an SP02 promoter, a penP promoter, etc. may be used; in the case of yeasts, a GAP promoter, a PH05 promoter, an ADH promoter, etc. may be used; and in the case of animal cells, an SV40 promoter, a CMV promoter, a retrovirus-derived promoter, etc. may be used.

When a host cell is to be transformed with the thus obtained vector containing a gene of interest, the host cell to be used may be bacterial (e.g. the genus *Escherichia* and the genus *Bacillus*), yeasts (the genus *Saccharomyces*, the genus *Pichia*, and the genus *Candida*), animal cells (CHO cell, COS cell, etc.), and the like. Liquid media are suitable as the culture medium and it is particularly preferred for them to contain the carbon sources, nitrogen sources and other nutrients that are required for the growth of the transformed cell being cultured. If desired, vitamins, growth promoting factors, sera, etc. may be added. In order to purify the compound of the present invention from the culture medium containing the peptide derivative of the present invention, the same separating/purifying procedures as those used to obtain peptide compounds by chemical synthesis may be employed.

The compounds of the present invention can be used to treat diseases that involve functional abnormalities in the gastrointestinal tract (for example, conditions that are characterized by a drop in the baseline of gastrointestinal motility activity). Functional abnormalities in the gastrointestinal tract are conditions that present uncomfortable symptoms in the gastrointestinal tract although no apparent organic abnormalities such as inflammations and ulcers are detected by endoscopy, blood testing, etc. and a group of diseases that are collectively called "functional gastrointestinal disorders" are finely classified and defined by their symptoms according to the ROME III criteria (Gastroenterology 130: 1377-1556, 2006). Diseases that involve functional abnormalities in the gastrointestinal tract include such conditions as functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, and post-operative ileus.

It should be mentioned that functional abnormalities in the gastrointestinal tract are diagnosed not only by subjective symptoms such as abdominal pain, nausea, vomiting, diarrhea, constipation, heartburn, abdominal bloating, and poor appetite but also by objective assays such as measurement of the pressure in the gastrointestinal tract, gastric juice testing, gastric pH monitoring, gastric emptying assay, gastrointestinal X-ray analysis, and endoscopy.

The compounds of the present invention or pharmaceutically acceptable salts thereof can be used in animals including man in sufficient amounts to confer the desired gastrointestinal motility stimulating activity, either alone or in admixture with known, pharmaceutically acceptable carriers, excipients, fillers, etc.

For the purposes of the present invention, the pharmaceutically acceptable salts include, for example, salts with inorganic bases, salts with organic bases, salts with inorganic acids, salts with organic acids, and salts with basic or acidic amino acids, but these are not the sole examples and any common salts may be used.

The peptide compounds according to the present invention can also be administered by various routes of injection such as subcutaneous injection, intramuscular injection, and intravenous injection. In addition, since the peptide compounds according to the present invention provide high absorption upon transmucosal administration, they can be administered by transmucosal routes, namely non-injection routes such as oral, intranasal, pulmonary, transoromucosal, and transvaginal routes, as well as ocular instillation. Desirably, the compounds are administered orally, intranasally or pulmonarily, and most desirably, they are administered pulmonarily or intranasally.

When the present compounds are used to treat the diseases mentioned above, their dosage depends on the condition of the patient, the degree of the desired therapeutic effect, the route of administration, the frequency of administration, etc. and, in the case of administration to man, the dosage can be varied from a low level of 0.01 µg/kg. A preferred dosage may be 0.01-500 µg/kg, more preferably 0.05-100 µg/kg. Amounts in these ranges may be desirably administered 1-3 times per day.

The peptide compounds of the present invention or pharmaceutically acceptable salts thereof can be used in combination with pharmaceutically acceptable carriers. Pharmaceutically acceptable carriers that may be used include various organic or inorganic carrier substances that are conventional as pharmaceutical necessities and they are compounded as excipients, lubricants, binders, disintegrants, or the like in solid preparations, and as solvents, solubilizers, suspending agents, tonicity agents, buffers, antiseptics, antioxidants, or the like in liquid preparations. A typical example of excipients is lactose; typical examples of lubricants are talc and colloidal silica. Typical examples of solvents are water for injection, proline glycol, sesame oil, and corn oil; suspending agents include surfactants such as stearyl triethanolamine, sodium lauryl sulfate, laurylaminopropionic acid, lecithin, and glyceryl monostearate, but other common pharmaceutical necessities may of course be used.

EXAMPLES

On the following pages, the present invention is described more specifically by reference to working examples, comparative examples and the like but it should be understood that the present invention is by no means limited to the working examples.

The meanings of the main abbreviations used in the working examples are shown below.

Phg(C#CH$_2$): L-β-homophenylglycine
Ac-Nal: acetylnaphthylalanine
Sar: L-sarcosine
CH$_2$—NH: -psi[CH$_2$NH]— bond (also called a pseudo bond)
Fmoc: fluorenylmethyloxycarbonyl
Boc: t-butyloxycarbonyl
TFA: trifluoroacetic acid
Trt: trityl
HBTU: N-[(1H-benzotriazol-1-yl)dimethylaminomethylene)]-N-methylmethaneaminium N-oxide hexafluorophosphate
HOBt: 1-hydroxybenzotriazole DCC: N,N'-dicyclohexylcarbodiimide
TIPS: triisopropylsilane Synthesis of Compounds Considering the pathway of motilin degradation by the degradative enzyme, the stability of the 13th-position methionine, the retention of motilin's physiological activity, and other factors, the motilin-like peptide compounds identified below were synthesized. In addition, native motilin was synthesized as the reference for comparison. Comparative compounds 1 and 2, as well as present compounds 1-13 had the following amino acid sequences.

```
Native motilin:
                                            (SEQ ID NO: 1)
Phe Val Pro Ile Phe Thr Tyr Gly Glu Leu Gln Arg Met Gln Glu Lys Glu Arg Asn Lys Gly Gln;

Comparative compound 1 (13Leu-motilin):
                                            (SEQ ID NO: 16)
Phe Val Pro Ile Phe Thr Tyr Gly Glu Leu Gln Arg Leu Gln Glu Lys Glu Arg Asn Lys Gly Gln;

Comparative compound 2 (MT139):
                                            (SEQ ID NO: 17)
Phe*Val Pro Ile Phe Thr Tyr Gly Glu Leu Gln Arg Met Gln Glu Lys Glu Arg Asn Lys Gly Gln;

Compound 1 (MT095):
                                            (SEQ ID NO: 3)
Phe Val Pro Ile Phe Thr Tyr Gly Glu Leu Gln Arg Met Gln Glu Lys Glu Arg Asn Lys Pro Gln;

Compound 2 (MT114):
                                            (SEQ ID NO: 4)
Phe Val Pro Ile Phe Thr Tyr Gly Glu Leu Gln Arg Leu Gln Glu Lys Glu Arg Asn Lys Pro Gln;

Compound 3 (MT116):
                                            (SEQ ID NO: 5)
Phe Val Pro Ile Phe Thr Tyr Gly Asp Leu Gln Arg Leu Gln Glu Lys Glu Arg Pro Lys Pro Gln;

Compound 4 (MT124):
                                            (SEQ ID NO: 6)
Phg(C#CH2) Val Pro Ile Phe Thr Tyr Gly Glu Leu Gln Arg Leu Gln Glu Lys Glu Arg Pro Lys Pro Gln;

Compound 5 (MT126):
                                            (SEQ ID NO: 7)
Phg(C#CH2) Val Sar Ile Phe Thr Tyr Gly Glu Leu Gln Arg Leu Gln Glu Lys Glu Arg Pro Lys Pro Gln;

Compound 6 (MT140):
                                            (SEQ ID NO: 8)
Phe*Val Pro Ile Phe Thr Tyr Gly Glu Leu Gln Arg Met Gln Glu Lys Glu Arg Asn Lys Pro Gln;

Compound 7 (MT141):
                                            (SEQ ID NO: 9)
Phe*Val Pro Ile Phe Thr Tyr Gly Glu Leu Gln Arg Leu Gln Glu Lys Glu Arg Asn Lys Pro Gln;

Compound 8 (MT107):
                                            (SEQ ID NO: 10)
Phe Val Pro Ile Phe Thr Tyr Gly Glu Leu Gln Arg Met Gln Glu Lys Glu Arg Pro Lys Pro Gln;

Compound 9 (MT115):
                                            (SEQ ID NO: 11)
Phe Val Pro Ile Phe Thr Tyr Gly Glu Leu Gln Arg Leu Gln Glu Lys Glu Arg Pro Lys Pro Gln;

Compound 10 (M125):
                                            (SEQ ID NO: 12)
Phg(C#CH2) Val Sar Ile Phe Thr Tyr Gly Glu Leu Gln Arg Met Gln Glu Lys Glu Arg Pro Lys Pro Gln;

Compound 11 (MT128):
                                            (SEQ ID NO: 13)
Ac-Nal Val Pro Ile Phe Thr Tyr Gly Glu Leu Gln Arg Met Gln Glu Lys Glu Arg Asn Lys Pro Gln;

Compound 12 (MT154):
                                            (SEQ ID NO: 14)
Phe*Val Pro Ile Phe Thr Tyr Gly Asp Leu Gln Arg Leu Gln Glu Lys Glu Arg Pro Lys Pro Gln;

Compound 13 (MT155):
                                            (SEQ ID NO: 15)
Phe*Val Pro Ile Phe Thr Tyr Gly Asp Leu Gln Arg Met Gln Glu Lys Glu Arg Pro Lys Pro Gln.
```

If the -psi[$CH_2NH$]— bond is used as the bond between the first amino acid (corresponding to X1) and Val is used in any of the compounds identified above, the bond is represented by the asterisk (*).

To extend the peptide chain, a peptide synthesizer (433A, product of Applied Biosystems) was mainly used and a protected peptide derivative/resin was constructed by the Fmoc method and a Boc-amino acid was finally introduced at the N terminal end. The resulting protected peptide resin was deprotected with trifluoroacetic acid (TFA) or diluted TFA containing various scavengers and the liberated peptide was subjected to a purification procedure. By reverse-phase HPLC using a C18 column, both purification and purity check were performed; then, structure was verified by mass analysis.

The peptide compounds of the present invention can be synthesized by ordinary peptide synthesis methods; as typical examples, syntheses of compound 1 (MT095) and compound 6 (MT140) are described below.

Example 1

Synthesis of Compound 1 (MT095)

This example was conducted with a view to synthesizing compound 1 (MT095, SEQ ID NO: 3) chemically.

An Fmoc-Gln(Trt)-Alko resin (product of WATANABE CHEMICAL; 47.6 mg, 0.03 mmol) was treated with 20% piperazine for 20 minutes and then introduction of Fmoc-amino acids by means of HBTU/HOBt and Fmoc removal by means of piperazine were repeated, starting from the C terminal end of SEQ ID NO: 3 in a sequential manner to thereby construct an Fmoc-peptide-resin. Finally, Boc-Phe-OH was introduced by means of DCC/HOBt and to the resulting protected peptide resin, a deprotecting reagent (5.0 mL) containing not only 90% trifluoroacetic acid but also phenol, water and TIPS was added and the mixture was stirred for 2 hours at room temperature. The resin was filtered off and the filtrate was concentrated; thereafter, ether was added to the residue to form a precipitate. The precipitate was recovered by filtration and dried to give about 30 mg of a crude peptide product.

The crude peptide product was dissolved in 1.0 mL of 1 N acetic acid and after loading the solution on an Inertsil PREP ODS column (Φ20 mm×250 mm; product of GL Sciences, Inc.), elution was conducted at a linear gradient of 0% to 50% acetonitrile in 0.1% trifluoroacetic acid for 50 minutes (flow rate: 10 mL/min). With UV (220 nm) monitoring, the desired fractions were sorted to recover and freeze-dried to give about 5.0 mg of the end product.

The obtained end product was loaded on an Inertsil PREP ODS column (Φ4.6 mm×250 mm; product of GL Sciences, Inc.), elution was conducted at a linear gradient of 5% to 65% acetonitrile in 0.1% trifluoroacetic acid for 30 minutes (flow rate: 1.5 mL/min). By UV (220 nm) monitoring, the purity of the end product was measured.

The obtained end product was subjected to MALDI TOF-MS (Daltonics BIFLEX III, product of Bruker) for verification of its molecular weight and to an amino acid analysis (consisting of treatment in 6 N—HCl at 110° C. for 24 hours until the product was hydrolyzed to amino acids, which were respectively quantified by HPLC) to verify the peptide content. Measured value from MALDI-TOF MS: 2738.718 (theoretical, 2739.2); purity from analytical HPLC: 96.0%; peptide content by amino acid analysis: 643 μg/mg.

Example 2

Synthesis of Compound 6 (MT140)

This example was conducted with a view to synthesizing compound 6 (MT140, SEQ ID NO: 8) chemically.

An Fmoc-Gln(Trt)-Alko resin (product of WATANABE CHEMICAL; 47.6 mg, 0.03 mmol) was treated with 20% piperazine for 20 minutes and then introduction of Fmoc-amino acids by means of HBTU/HOBt and Fmoc removal by means of piperazine were repeated, starting from the C terminal end of SEQ ID NO: 8 in a sequential manner to thereby construct an Fmoc-peptide-resin. Finally, Boc-Phe aldehyde was introduced by means of sodium cyanotrihydroborate/1% acetic acid and to the resulting protected peptide resin, a deprotecting reagent (5.0 mL) containing not only 90% trifluoroacetic acid but also phenol, water and TIPS was added and the mixture was stirred for 2 hours at room temperature. The resin was filtered off and the filtrate was concentrated; thereafter, ether was added to the residue to form a precipitate. The precipitate was recovered by filtration and dried to give about 30 mg of a crude peptide product.

The crude product was dissolved in 1.0 mL of 1 N acetic acid and after loading the solution on an Inertsil PREP ODS column (Φ20 mm×250 mm; product of GL Sciences Inc.), elution was conducted at a linear gradient of 0% to 50% acetonitrile in 0.1% trifluoroacetic acid for 50 minutes (flow rate: 10 mL/min). With UV (220 nm) monitoring, the desired fractions were recovered and freeze-dried to give about 5.0 mg of the end product.

The obtained end product was loaded on an Inertsil PREP ODS column (Φ4.6 mm×250 mm; product of GL Sciences Inc.), elution was conducted at a linear gradient of 5% to 65% acetonitrile in 0.1% trifluoroacetic acid for 30 minutes (flow rate: 1.5 mL/min). By UV (220 nm) monitoring, the purity of the end product was measured.

The obtained end product was subjected to MALDI TOF-MS (Daltonics BIFLEX III, product of Bruker) for verification of its molecular weight. Measured value from MALDI-TOF MS: 2725.040 (theoretical, 2725.2); purity from analytical HPLC: 98.7%; peptide content by amino acid analysis: 707 μg/mg.

By similar techniques, native motilin as well as compounds 1-13 (of SEQ ID NOS: 3-15, respectively) and comparative compounds 1 and 2 (of SEQ ID NOS: 16 and 17, respectively) were produced. Their MS values are listed in Table 1 together with the peptide values as determined by amino acid analysis.

TABLE 1

Table 1: MS Values and Peptide Contents of Compounds

| Compound name | Structure | Peptide content (%) (Amino acid analysis) | Measured MS values (Theoretical) |
|---|---|---|---|
| Native motilin | FVPIFTYGELQRMQEKERNKGQ (SEQ ID NO: 1) | 88.6 | 2698.382 (2699.1) |
| Comparative compound 1 ($^{13}$Leu-motilin) | FVPIFTYGELQRLQEKERNKGQ (SEQ ID NO: 16) | 73.1 | 2680.432 (2681.0) |
| Comparative compound 2 (MT139) | F*VPIFTYGELQRMQEKERNKGQ (SEQ ID NO: 17) | 71.8 | 2683.998 (2685.1) |
| Compound 1 (MT095) | FVPIFTYGELQRMQEKERNKGQ (SEQ ID NO: 3) | 64.3 | 2738.718 (2739.2) |
| Compound 2 (MT114) | FVPIFTYGELQRLQEKERNKPQ (SEQ ID NO: 4) | 75.8 | 2720.544 (2721.1) |
| Compound 3 (MT116) | FVPIFTYGDLQRLQEKERPKPQ (SEQ ID NO: 5) | 76.8 | 2689.574 (2690.1) |
| Compound 4 (MT124) | Phg(C#CH$_2$)-VPIFTYGELQRLQEKERPKPQ (SEQ ID NO: 6) | 75.7 | 2703.920 (2704.1) |
| Compound 5 (MT126) | Phg(C#CH$_2$)-V-Sar-IFTYGELQRLQEKERPKPQ (SEQ ID NO: 7) | 58.3 | 2677.60 (2677.0) |

TABLE 1-continued

Table 1: MS Values and Peptide Contents of Compounds

| Compound name | Structure | Peptide content (%) (Amino acid analysis) | Measured MS values (Theoretical) |
|---|---|---|---|
| Compound 6 (MT140) | F*VPIFTYGELQRMQEKERNKPQ (SEQ ID NO: 8) | 70.7 | 2725.040 (2725.2) |
| Compound 7 (MT141) | F*VPIFTYGELQRLQEKERNKPQ (SEQ ID NO: 9) | 70.3 | 2706.980 (2707.1) |
| Compound 8 (MT107) | FVPIFTYGELQRMQEKERPKPQ (SEQ ID NO: 10) | — | 2721.272 (2722.2) |
| Compound 9 (MT115) | FVPIFTYGELQRLQEKERPKPQ (SEQ ID NO: 11) | — | 2703.463 (2704.1) |
| Compound 10 (MT125) | Phg(C#CH$_2$)-V-Sar-IFTYGELQRMQEKERPKPQ (SEQ ID NO: 12) | — | 2695.845 (2695.1) |
| Compound 11 (MT128) | Ac-Nal-VPIFTYGELQRMQEKERNKPQ (SEQ ID NO: 13) | — | 2830.62 (2831.2) |
| Compound 12 (MT154) | F*VPIFTYGDLQRLQEKERPKPQ (SEQ ID NO: 14) | — | 2676.598 (2676.1) |
| Compound 13 (MT155) | F*VPIFTYGDLQRMQEKERPKPQ (SEQ ID NO: 15) | — | 2693.923 (2694.2) |

Notes:
Amino acid content was not measured for compounds 8-13. The asterisk (*) in the structures of comparative compound 2 as well as compounds 6, 7, 12 and 13 indicates that the bond between adjacent amino acids is a -psi[CH$_2$NH]- bond.

Example 3

Measurement of Fasting IMC Inducing Activity

This example was conducted with a view to measuring the fasting IMC inducing activity in the dog's body of the compounds prepared by the methods described in Examples 1 and 2.

In accordance with the method of ITOH et al. (Zen Itoh et al, Gastroenterologia Japonica 12; 275-283, 1977), the fasting IMC inducing activity of the compounds was evaluated by measuring the contractile movement of a conscious dog's gastrointestinal tract to which force transducers had been sutured. More specifically, dogs under anesthesia were subjected to a surgical operation in which force transducers were sutured to the serous membranes of the gastric antrum, duodenum, jejunum and ileum along the ring-shaped muscle and, thereafter, the strain from each transducer was sent to a recorder via an amplifier.

About 10 minutes after the end of spontaneous IMC in the fasting period (10 minutes after strong contractions of the stomach), conscious dogs were rapidly injected intravenously with 0.1 µg/kg of native motilin or selected motilin derivative compounds and the resulting gastrointestinal contractile movements were observed. The administered test compounds induced strong contractions of the stomach and their propagation to the duodenum was defined as IMC; a compound was evaluated as "positive in IMC inducing activity" when it induced IMC at a dose of 0.1 µg/kg.

FIG. 1 depicts patterns for the fasting IMC inducing activity as observed when native motilin as well as compound 4 (MT124) and compound 6 (MT140) were intravenously administered at a dose of 0.1 µg/kg, and Table 2 shows the results of checking native motilin and selected motilin derivative compounds for the fasting IMC inducing activity. In FIG. 1, the arrows indicate the timing on which native motilin as well as compounds 4 and 6 were administered. As shown in FIG. 1, the gastric antrum started to contract when the native motilin was administered (at the point in time indicated by ↑) and the contraction continued for about 10 minutes. Immediately after its start in the gastric antrum, the contraction propagated to the duodenum which, like the gastric antrum, continued to contract for about 10 minutes. When compound 4 (MT124) and compound 6 (MT140) were administered intravenously, contractions occurred in the same pattern as described above for the administration of native motilin. As is also clear from FIG. 1 and Table 2, not only native motilin and compound 4 (MT124) and compound 6 (MT140) but also any other motilin derivative compounds of the present invention induced fasting IMC similar to spontaneous IMC and its intensity was almost comparable to that of IMC induced by the native motilin.

TABLE 2

Fasting IMC Inducing Activity in Dogs Administered Intravenously with Native Motilin and Motilin Derivatives

| Compound name | Dose (µg/kg) | IMC Inducing activity |
|---|---|---|
| Native motilin | 0.1 | Positive |
| Comparative compound 1 ($^{13}$Leu-motilin) | 0.1 | Positive |
| Comparative compound 2 (MT139) | 0.1 | Positive |
| Compound 1 (MT095) | 0.1 | Positive |
| Compound 2 (MT114) | 0.1 | Positive |
| Compound 3 (MT116) | 0.1 | Positive e |
| Compound 4 (MT124) | 0.1 | Positive |

TABLE 2-continued

Fasting IMC Inducing Activity in Dogs Administered
Intravenously with Native Motilin and Motilin Derivatives

| Compound name | Dose (μg/kg) | IMC Inducing activity |
|---|---|---|
| Compound 5 (MT126) | 0.1 | Positive |
| Compound 6 (MT140) | 0.1 | Positive |
| Compound 7 (MT141) | 0.1 | Positive |
| Compound 8 (MT107) | 0.1 | Positive |
| Compound 9 (MT115) | 0.1 | Positive |
| Compound 10 (MT125) | 0.1 | Positive |

From these results, it became clear that all compounds that were prepared in Examples 1 and 2 had the same level of fasting IMC inducing activity as native motilin.

Comparative Example 1

Pharmacokinetic Experiment on Intravenously Administered Native Motilin in Rats

Native motilin was administered intravenously to rats and its plasma levels were measured.

Intravenous administration was performed on rats that had a polyethylene tube (PE-50; product of Clay Adams) preliminarily inserted into the femoral artery. As test animals, 7-wk old male SD rats (purchased from CHARLES RIVER LABORATORIES JAPAN, INC.) that consisted of 3 rats per a group were subjected to the following experiment. Native motilin was dissolved in a 5% mannitol solution to prepare a solution at a concentration of 100 μg/mL and this solution was administered to each rat at a dose of 1 mL/kg through the tail vein by means of a syringe and a 26G needle (both being products of TERUMO). Before administration and 1, 3, 5, 10, 20, 30 and 60 minutes after administration, blood was sampled through the polyethylene tube inserted into the femoral artery.

To the collected blood sample, a 10% $EDTA.2Na.2H_2O$ solution was immediately added at a volume ratio of 1:100 and the plasma was separated by centrifugation. The plasma was immediately mixed with a 5,000 IU/mL aprotinin solution at a volume ratio of 1:10 and stored at −80° C. until use in measurement.

Measurement of the plasma concentration of native motilin was conducted by the radioimmunoassay (RIA) technique using an anti-motilin antibody. Stated more specifically, after adding an anti-motilin antibody to the plasma sample, [$^{125}$I-Tyr7] motilin was added for a competitive reaction to take place. By subsequent addition of a secondary antibody, the motilin binding to the anti-motilin antibody was precipitated and after separating the supernatant, the radioactivity in the precipitating faction was measured with a γ-counter (product of PerkinElmer).

Figure 2:
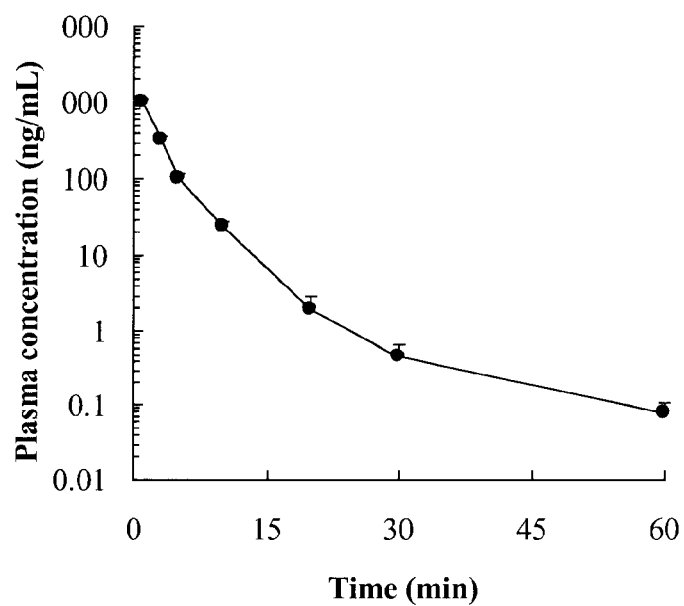
FIG. 2 is a graph showing a profile of plasma levels in rats that were intravenously administered with native motilin.

The obtained profile of the concentration of native motilin in plasma is depicted in FIG. 2. From this profile, the plasma concentration at time zero (C0) and the area under curve for plasma concentrations (AUC) were calculated as pharmacokinetic parameters; C0 was determined by extrapolation and AUC by the trapezoidal method. The values of C0 and AUC that resulted from intravenous administration of native motilin at a dose of 100 μg/kg were calculated to be 1797 ng/mL and 3598 ng·min/mL, respectively.

Example 4

Pharmacokinetic Experiment on Pulmonarily Administered Native Motilin and Motilin Derivative Compounds in Rats This example was conducted with a view to measuring by RIA the changes that occurred in rats in terms of the plasma concentrations of pulmonarily administered native motilin and motilin derivative compounds. When the RIA technique is applied, all substances that react with the anti-motilin antibody are detected, so aside from unaltered forms, metabolites that react with the antibody are also likely to be detected. Thus, after pulmonary administration of native motilin and motilin derivative compounds into rats, the collected plasma was fractionated by HPLC and the immunological activity in each fraction was measured to demonstrate that the substance reacting with the antibody was in an unaltered form, which verified the suitability of the RIA technique as a method to measure the changes in plasma concentration.

To be more specific, a polyethylene tube (PE-240; product of Clay Adams) was inserted into the trachea of 7-wk old male SD rats (purchased from CHARLES RIVER LABORATORIES JAPAN, INC.); native motilin or compound 2 (MT114) was dissolved in an aqueous solution of 0.1 N acetic acid to prepare a solution at a concentration of 1 mg/mL and 25 μL of the solution was administered into the polyethylene tube through the trachea by means of an intratracheal liquid spraying device (MicroSprayer; product of Penn Century). Five minutes after the administration, blood was sampled through the abdominal aorta and treated as in Comparative Example 1 to separate plasma. After pretreatment with a Sep-Pak C18 cartridge (product of Waters), the plasma was fractionated by being injected into HPLC (LC-10A; product of Shimadzu Corporation) equipped with Cosmosil 5C18 column (product of nacalai tesque). For each sample, an eluate was sampled at one-minute intervals from just after the sample injection to a 40-minute after sample injection and the immunological activity in each fraction was measured by RIA. As a result, in each of the plasma samples, an immunological activity peak was detected only at the elution point corresponding to the administered compound (in unaltered form) and no other peaks were observed. Since these results suggest that the compound detected in plasma after pulmonary administration was in an unaltered form with a very small likelihood for the presence of metabolites, the RIA technique was shown to be suitable as an assay method for use in the example under consideration.

Pulmonary administration of samples was also performed as described above using rats that had a polyethylene tube preliminarily inserted into the femoral artery. As test animals, 7- to 10-wk old male SD rats (purchased from CHARLES RIVER LABORATORIES JAPAN, INC.) that consisted of 3 rats per a group were subjected to the following experiment. Native motilin or motilin derivative compounds were dissolved in an aqueous solution of 0.1 N acetic acid to prepare a solution at a concentration of 1 mg/mL and 25 μL of the solution was administered into the polyethylene tube through the trachea by means of an intratracheal liquid spraying device (MicroSprayer; product of Penn Century). Before administration and 5, 10, 20, 30 and 60 minutes after administration, blood was sampled through the polyethylene tube inserted into the femoral artery. The collected blood sample was treated as in Comparative Example 1 to separate plasma and the concentrations of native motilin and motilin derivative compounds in plasma were measured by RIA. In the measurement, the respective derivatives were used as standard substances to construct calibration curves for determining the plasma levels.

Figure 3:
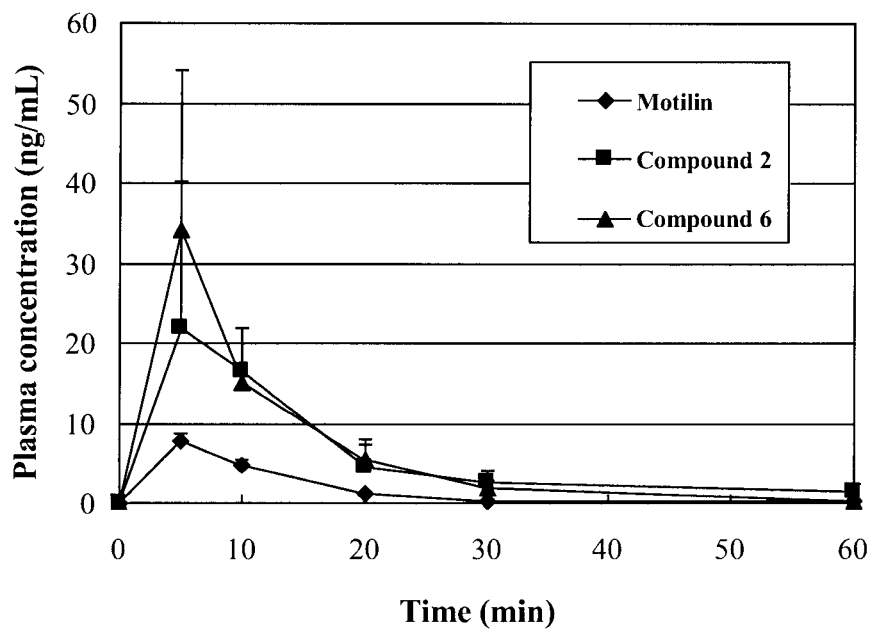
FIG. 3 is a graph showing profiles of plasma levels after pulmonary administration of native motilin, compound 2 (MT 114) and compound 6 (MT 140).

The profiles for the plasma concentrations of native motilin as well as compound 2 (MT114) and compound 6 (MT140) after pulmonary administration are shown in FIG. 3. As is also clear from FIG. 3, compared with the profile of motilin concentration in plasma after pulmonary administration of the native motilin to the rats, the plasma concentrations of compound 2 (MT114) and compound 6 (MT140) after pulmonary administration to the rats had high peak levels, showing that those compounds could maintain higher in vivo concentrations for a longer period than the native motilin.

On the basis of the profiles for native motilin or motilin derivative compounds in plasma as obtained by the tests described above, a maximum plasma concentration (Cmax) and the area under curve for plasma concentrations (AUC) were calculated as pharmacokinetic parameters; Cmax was determined from observed values and AUC by the trapezoidal method. Using these values, bioavailability (BA (%)) was calculated by the following equation:

$$BA(\%) = [(AUC/Dose)/(AUC(motilin\_iv)/Dose(motilin\_iv))] \times 100$$

AUC: AUC (ng·min/mL) after pulmonary administration
Dose: dose (µg/kg) in pulmonary administration
AUC (motilin_iv): AUC (ng·min/mL) after intravenous administration of native motilin
Dose (motilin_iv): dose (µg/kg) in intravenous administration of native motilin.

The pharmacokinetic parameters of native motilin and motilin derivative compounds are shown in Table 3 below.

As is clear from the data shown in Table 3, the bioavailability (hereinafter abbreviated as BA) of compound 1 (with proline substituted for glycine as the amino acid at position 21 of native motilin; $^{21}$Pro-motilin; SEQ ID NO: 3) was 5.3% upon pulmonary administration to rats and this value was higher than the BA which was achieved by native motilin upon pulmonary administration (3.3%). Compound 2 (with leucine substituted for methionine as the amino acid at position 13 of native motilin, and with proline substituted for the 21-position amino acid; $^{13}$Leu-, $^{21}$Pro-motilin; SEQ ID NO: 4) had BA of 10.4% upon pulmonary administration to rats, a marked improvement over comparative compound 1 ($^3$Leu-motilin; SEQ ID NO: 16) (2.8%). Further in addition, compound 6 (-psi[CH$_2$NH]— bond; $^{21}$Pro-motilin; SEQ ID NO: 8) had BA of 11.5% upon pulmonary administration, a marked improvement over comparative compound 2 (-psi[CH$_2$NH]-motilin; SEQ ID NO: 17) (4.1%). In summary, compounds 1-13 which were motilin derivatives with a substitution of proline at position 21 had BA values of 5.3-18.7%, all being improved over the BA of native motilin (3.3%). From these results, absorbability upon pulmonary administration was found to improve when proline was substituted for the amino acid at position 21 of native motilin or motilin-like peptide compounds.

Thus, when compounds 1-13, i.e., motilin derivatives with a substitution of proline at position 21, were administered pulmonarily to rats, the efficiency of absorption into the body through the mucous membrane improved so markedly (see Table 3) that the in vivo concentrations of the absorbed compounds were shown to be maintained at higher levels for a longer period than that of native motilin.

TABLE 3

Pharmacokinetic Parameters of Pulmonarily Administered Native Motilin and Motilin Derivative Compounds in Rats

| Compound name | Dose (µg/rat) | Dose (µg/kg) | Cmax (ng/mL) | AUC (ng · min/mL) | BA (%) |
|---|---|---|---|---|---|
| Native motilin | 25 | 80.7 ± 2.6 | 7.84 ± 0.98 | 94.9 ± 5.7 | 3.3 ± 0.1 |
| Comparative compound 1 ($^{13}$Leu-motilin) | 25 | 62.5 ± 0.0 | 4.53 ± 2.86 | 63.3 ± 36.6 | 2.8 ± 1.6 |
| Comparative compound 2 (MT139) | 25 | 81.6 ± 3.0 | 9.30 ± 3.09 | 118.6 ± 41.0 | 4.1 ± 1.6 |
| Compound 1 (MT095) | 25 | 62.6 ± 2.6 | 9.09 ± 0.53 | 119.3 ± 15.0 | 5.3 ± 0.6 |
| Compound 2 (MT114) | 25 | 92.7 ± 3.4 | 26.60 ± 11.30 | 350.4 ± 146.6 | 10.4 ± 4.3 |
| Compound 3 (MT116) | 25 | 82.4 ± 1.6 | 24.60 ± 5.80 | 281.8 ± 24.0 | 9.5 ± 0.9 |
| Compound 4 (MT124) | 25 | 70.4 ± 9.9 | 14.61 ± 8.23 | 281.3 ± 201.7 | 11.0 ± 7.2 |
| Compound 5 (MT126) | 25 | 86.2 ± 0.0 | 14.81 ± 7.78 | 175.3 ± 90.7 | 5.7 ± 2.9 |
| Compound 6 (MT140) | 25 | 92.7 ± 3.4 | 34.22 ± 19.97 | 380.4 ± 191.5 | 11.5 ± 6.1 |
| Compound 7 (MT141) | 25 | 83.5 ± 4.7 | 17.20 ± 7.18 | 194.3 ± 47.9 | 6.4 ± 1.3 |
| Compound 9 (MT115) | 25 | 56.4 ± 1.5 | 8.99 ± 5.99 | 115.5 ± 64.2 | 5.7 ± 3.1 |
| Compound 10 (MT125) | 25 | 89.3 ± 0.0 | 6.10 ± 1.50 | 189.5 ± 25.5 | 5.9 ± 0.8 |
| Compound 12 (MT154) | 25 | 83.6 ± 5.6 | 30.09 ± 15.79 | 565.3 ± 341.1 | 18.7 ± 10.7 |
| Compound 13 (MT155) | 25 | 91.5 ± 1.9 | 18.42 ± 10.40 | 185.4 ± 48.5 | 5.6 ± 1.5 |

Comparative Example 2

Pharmacokinetic Experiment on Intravenously Administered Native Motilin and Motilin Derivative Compound in Monkeys In this example, native motilin and a motilin derivative compound were administered intravenously to monkeys and their plasma concentrations were measured.

As test animals, 8- to 9-year old male cynomolgus monkeys (N=1-2 per group) were subjected to the following experiment. Native motilin and compound 2 were each dissolved in a 5% mannitol solution to prepare solutions at a concentration of 100 µg/mL; the solutions were administered to the animals at a dose of 0.1 mL/kg through the right cephalic vein by means of a syringe and a needle (both being products of TERUMO). Before administration and 5, 10, 15, 20, 30 and 60 minutes after administration, blood was sampled through the left cephalic vein.

To the collected sample, a 10% EDTA.2Na.2H$_2$O solution was immediately added at a volume ratio of 1:100 and the plasma was separated by centrifugation. The plasma was immediately mixed with a 5,000 IU/mL aprotinin solution at a volume ratio of 1:10 and stored at −80° C. until use in measurement.

Measurement of the plasma concentrations of native motilin and the motilin derivative compound was conducted by the radioimmunoassay (RIA) technique using an anti-motilin antibody. Stated more specifically, after adding an anti-motilin antibody to the plasma sample, [$^{125}$I-Tyr7] motilin was added for a competitive reaction to take place. By subsequent addition of a secondary antibody, the motilin binding to the anti-motilin antibody was precipitated and after separating the supernatant, the radioactivity in the precipitating faction was measured with a γ-counter (product of PerkinElmer).

Figure 4:
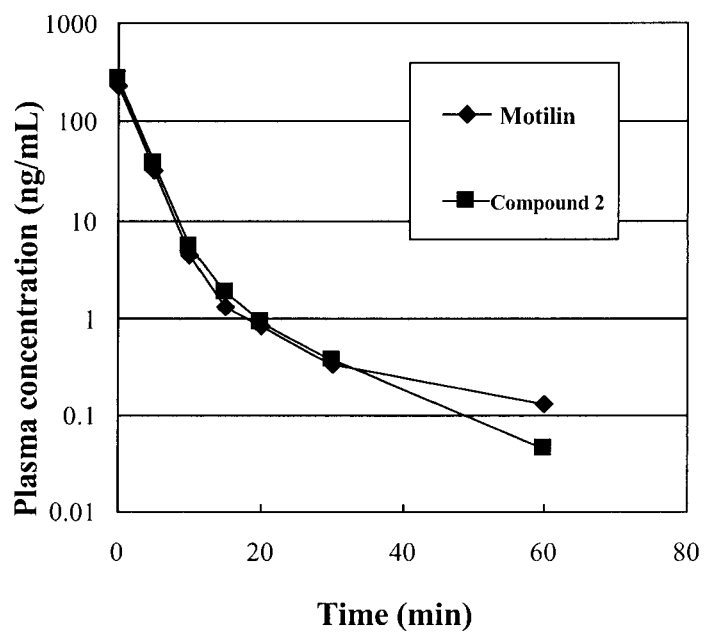
FIG. 4 is a graph showing profiles of plasma levels in monkeys that were intravenously administered with native motilin and compound 2 (MT 114).

The obtained profile of the concentration of native motilin in plasma is depicted in FIG. 4. From the obtained profiles for the plasma concentrations of native motilin and the motilin derivative compound, the plasma concentration at time zero (C0) and the area under curve for plasma concentrations (AUC) were calculated as pharmacokinetic parameters; C0 was determined by extrapolation and AUC by the trapezoidal method. The values of C0 and AUC that resulted from intravenous administration of native motilin at a dose of 10 µg/kg were calculated to be 233 ng/mL and 786 ng·min/mL, respectively, and the counterparts for compound 2 were 273 ng/mL and 926 ng·min/mL.

Example 5

Pharmacokinetic Experiment on Intranasally Administered Native Motilin and a Motilin Derivative Compound in Monkeys This example was conducted with a view to measuring by RIA the changes that occurred in monkeys in terms of the plasma concentrations of transnasally administered native motilin and a motilin derivative compound.

In the experiment, 10- to 11-year old male cynomolgus monkeys were used. Native motilin or compound 2 and microcrystalline cellulose were mixed at a ratio of 1:40 to prepare intranasal preparations, 20-mg portions of which were filled into gelatin capsules. Each capsule was administered into the right nasal cavity of each animal by means of an intranasal administration device (product of Hitachi Automotive Systems, Ltd.). Before administration and 5, 10, 15, 20, 30, 60, 120 and 180 minutes after administration, blood was sampled through the cephalic vein. The collected blood sample was treated as in Comparative Example 2 to separate plasma and the concentrations of native motilin and the motilin derivative compound in plasma were measured by RIA. In the measurement, the respective derivatives were used as standard substances to construct calibration curves for determining the plasma levels.

Figure 5:
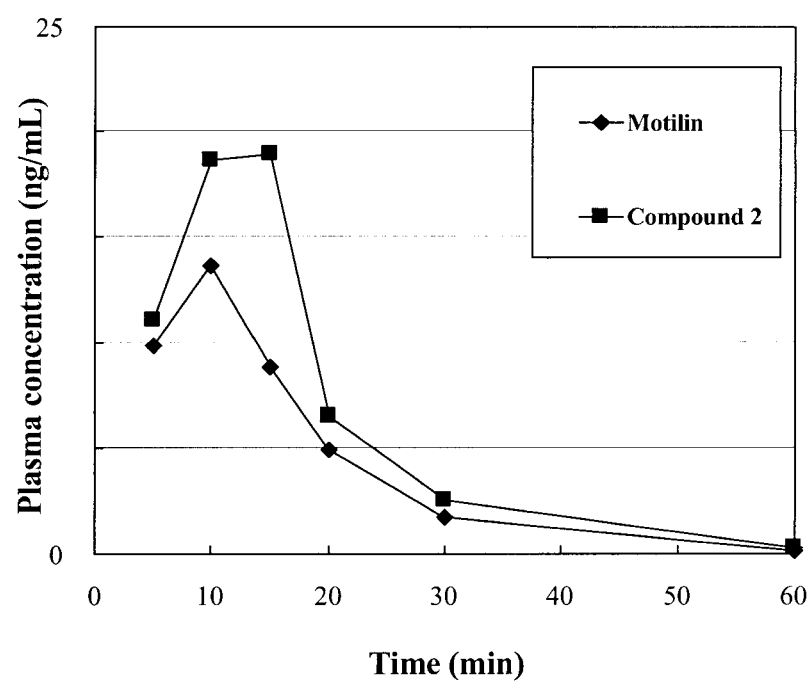
FIG. 5 is a graph showing profiles of plasma levels in monkeys that were intranasally administered with native motilin and compound 2 (MT 114).

The profiles for the plasma concentrations of native motilin and compound 2 (MT114) in the monkeys after intranasal administration are shown in FIG. 5. As is also clear from FIG. 5, compared with the profile of motilin concentration in plasma after intranasal administration of the native motilin to the monkeys, the plasma concentration of compound 2 (MT114) after intranasal administration to the monkeys had a high peak level, showing that the compound could maintain a higher in vivo concentration for a longer period than the native motilin.

On the basis of the profiles for native motilin and the motilin derivative compound in plasma as obtained by the tests described above, a maximum plasma concentration (Cmax) and the area under curve for plasma concentrations (AUC) were calculated as pharmacokinetic parameters; Cmax was determined from observed values and AUC by the trapezoidal method. Using these values, bioavailability (BA (%)) was calculated by the following equation:

$$BA(\%) = [(AUC/Dose)/(AUC(iv)/Dose(iv))] \times 100$$

AUC: AUC (ng·min/mL) after intranasal administration
Dose: dose (µg/kg) in intranasal administration
AUC (iv): AUC (ng·min/mL) after intravenous administration of each compound
Dose (iv): dose (µg/kg) in intravenous administration of each compound.

The pharmacokinetic parameters of native motilin and the motilin derivative compound are shown in Table 4 below.

TABLE 4

Pharmacokinetic Parameters of Intranasally Administered Native Motilin and A Motilin Derivative Compound in Monkeys (Mean for N = 1-2)

| Compound name | Dose (µg/monkey) | Dose (µg/kg) | Cmax (ng/mL) | AUC (ng · min/mL) | BA (%) |
|---|---|---|---|---|---|
| Native motilin | 523 | 85.0 | 13.6 | 241 | 3.6 |
| Compound 2 (MT114) | 540 | 80.6 | 23.5 | 361 | 5.1 |

As is clear from the data shown in Table 4, the bioavailability (hereinafter abbreviated as BA) of compound 2 was 5.1% upon intranasal administration to monkeys and this value was higher than the BA which was achieved by native motilin upon intranasal administration (3.6%). Thus, when compound 2 or a motilin derivative with a substitution of proline at position 21 was administered intranasally to monkeys, the efficiency of absorption into the body through the mucous membrane improved so markedly that the in vivo concentration of the absorbed compound was shown to be maintained at a higher level for a longer period than that of native motilin.

Industrial Applicability

The present invention relates to novel motilin-like peptide compounds. The motilin-like peptide compounds of the present invention or pharmaceutically acceptable salts thereof have effective gastrointestinal motility stimulating activity and higher absorbability upon transmucosal administration, so they can be used to treat diseases caused by functional abnormalities in the gastrointestinal tract (for example, conditions characterized by a drop in the baseline of gastrointestinal motility activity.) Diseases caused by functional abnormalities in the gastrointestinal tract include conditions such as functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, and post-operative ileus. The conventional peptidic motilin agonists including native motilin have been applicable only by direct intravenous injection but the compounds of the present invention can be administered via transmucosal and other non-intravenous routes and can reduce the burden on patients. Therefore, the present invention offers great industrial utility over the prior art.

Sequence Listing Free Text

SEQ ID NO: 1 is the amino acid sequence of human motilin.

SEQ ID NO: 2 is the amino acid sequence of a motilin analog.

SEQ ID NO: 3 is the amino acid sequence of compound 1 (MT095).

SEQ ID NO: 4 is the amino acid sequence of compound 2 (MT114).

SEQ ID NO: 5 is the amino acid sequence of compound 3 (MT116).

SEQ ID NO: 6 is the amino acid sequence of compound 4 (MT124).

SEQ ID NO: 7 is the amino acid sequence of compound 5 (MT126).

SEQ ID NO: 8 is the amino acid sequence of compound 6 (MT140).

SEQ ID NO: 9 is the amino acid sequence of compound 7 (MT141).

SEQ ID NO: 10 is the amino acid sequence of compound 8 (MT107).

SEQ ID NO: 11 is the amino acid sequence of compound 9 (MT115).

SEQ ID NO: 12 is the amino acid sequence of compound 10 (MT125).

SEQ ID NO: 13 is the amino acid sequence of compound 11 (MT128).

SEQ ID NO: 14 is the amino acid sequence of compound 12 (MT154).

SEQ ID NO: 15 is the amino acid sequence of compound 13 (MT155).

SEQ ID NO: 16 is the amino acid sequence of comparative compound 1 ($^{13}$Leu-motilin).

SEQ ID NO: 17 is the amino acid sequence of comparative compound 2 (MT139).

The invention claimed is:

1. A compound comprising the sequence of the SEQ ID NO: 2:

X1Val X2Ile Phe Thr Tyr Gly X3Leu Gln Arg X4Gln Glu Lys Glu Arg X5Lys Pro Gln, wherein all bonds between amino acids, except the X1-Val bond, are amide bonds;
the X1-Val bond is an amide bond or a -psi[CH$_2$—NH]- bond
wherein
X1 is an aromatic amino acid or a heteroaromatic amino acid;
X2 is proline or sarcosine;
X3 is glutamic acid or aspartic acid;
X4 is methionine or leucine;
X5 is asparagine or proline;
or a pharmaceutically acceptable salt thereof.

2. The compound or pharmaceutically acceptable salt thereof according to claim 1, wherein X1 is phenylalanine or β-homophenylglycine.

3. A compound comprising a sequence selected from SEQ ID NOs: 3 to 15 or a pharmaceutically acceptable salt thereof.

4. A pharmaceutical composition comprising the compound or pharmaceutically acceptable salt thereof according to claim 1.

5. A method for treating a disease associated with a functional abnormality in the gastrointestinal tract comprising administering the pharmaceutical composition according to claim 4, wherein the disease is selected from functional dyspepsia, diabetic gastroparesis, gastro-esophageal reflux disease, irritable bowel syndrome, small intestinal bacterial overgrowth, colonic pseudo-obstruction, paralytic ileus, chronic idiopathic intestinal pseudo-obstruction, or post-operative ileus.

6. The method according to claim 5, wherein the method comprises transmucosal administration.

7. The method according to claim 6, wherein the transmucosal administration is pulmonary or intranasal administration.

8. The pharmaceutical composition according to claim 4, wherein the pharmaceutical composition further comprises a carrier suitable for transmucosal administration.

* * * * *